(12) United States Patent
Birdsley et al.

(10) Patent No.: US 6,428,718 B1
(45) Date of Patent: Aug. 6, 2002

(54) SELECTIVE BACK SIDE WET ETCH

(75) Inventors: Jeffrey Birdsley, Cedar Park; Brennan Davis, Austin, both of TX (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 0 days.

(21) Appl. No.: 09/383,670

(22) Filed: Aug. 26, 1999

(51) Int. Cl.$^7$ .......................... H01L 21/302; B44C 1/22
(52) U.S. Cl. ........................ 216/84; 216/99; 438/7; 438/8; 438/16; 438/745; 438/750; 438/753
(58) Field of Search ..................... 438/745, 750, 438/753, 7, 8, 16; 216/99, 84

(56) References Cited

U.S. PATENT DOCUMENTS

| | | | | |
|---|---|---|---|---|
| 4,465,549 A | * | 8/1984 | Ritzman | 156/630 |
| 5,064,498 A | * | 11/1991 | Miller | 156/626 |
| 5,071,510 A | * | 12/1991 | Findler et al. | 156/647 |
| 5,086,011 A | | 2/1992 | Shiota | |
| 6,168,960 B1 | * | 1/2001 | Li | 438/14 |
| 6,352,871 B1 | * | 3/2002 | Goruganthu et al. | 438/18 |

OTHER PUBLICATIONS

Thong, J.T.L., Choi, W.K., Chong, C.W., *TMAH Etching of Silicon and the Interaction of Etching Parameters*, 1997, pp. 1–7.
Material Satefy Data Sheet—Tetramethylammonium hydroxide, 25% (Aqueous solution) pp. 1–5.
Malberti, P., Ciappa, M., Scacco, P., *A New Back–Etch for Silicon Devices*, 1997, pp. 257–261.

* cited by examiner

Primary Examiner—George Goudreau

(57) ABSTRACT

According to an example embodiment, a semiconductor device having a back side and a circuit side opposite the back side is analyzed. The semiconductor device includes bulk silicon in the back side and also includes epitaxial silicon. A wet etch solution comprising aqueous tetramethylammonium hydroxide (TMAHW) is directed at the back side. Using the wet etch solution, the back side is selectively etched and an exposed region is formed. The etching is selective to the bulk silicon. When the etching process encounters the epitaxial silicon, the etch rate slows and is used as an endpoint indicator of the selective etching process. Once the etching process is stopped, the circuitry is accessed via the exposed region.

19 Claims, 3 Drawing Sheets

SELECTIVE BACK SIDE WET ETCH

FIELD OF THE INVENTION

The present invention relates generally to semiconductor devices and their fabrication and, more particularly, to semiconductor devices and their manufacture involving selective wet etching.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

To increase the number of pad sites available for a die, to reduce the electrical path to the pad sites, and to address other problems, various chip packaging techniques have been developed. One of these techniques is referred to as controlled collapse chip connection or "flip-chip" packaging. With packaging technology, bonding pads of the die include metal (solder) bumps. Electrical connection to the package is made when the die is "flipped" over and soldered to the package. Each bump connects to a corresponding package inner lead. The resulting packages are low profile and have low electrical resistance and a short electrical path. The output terminals of the package, which are sometimes ball-shaped conductive bump contacts, are typically disposed in a rectangular array. These packages are occasionally referred to as "Ball Grid Array" (BGA) packages. Alternatively, the output terminals of the package may be pins and such packages are commonly known as pin grid array (PGA) packages.

Once the die is attached to such a package the back side portion of the die remains exposed. The transistors and other circuitry are generally formed in a very thin epitaxially-grown silicon layer on a single crystal silicon wafer from which the die is singulated. The side of the die including the epitaxial layer containing the transistors and other circuitry is often referred to as the circuit side or front side of the die. The circuit side of the die is positioned very near the package and opposes the back side of the die. Between the back side and the circuit side of the die is bulk silicon.

The positioning of the circuit side near the package provides many of the advantages of the flip chip. However, in some instances orienting the die with the circuit side face down on a substrate is disadvantageous. Due to this orientation of the die, the transistors and circuitry near the circuit side are not directly accessible for testing, modification or other purposes. Therefore, access to the transistors and circuitry near the circuit side is from the back side of the chip.

For flip-chips and other dies requiring or benefiting from back side access, techniques have been developed to access the circuit even though the integrated circuit (IC) is buried under the bulk silicon. For example, near-infrared (nIR) microscopy is capable of imaging the circuit because silicon is relatively transparent in these wavelengths of the radiation. However, because of the absorption losses of nIR radiation in silicon, it is generally required to thin the die to less than 100 microns in order to view the circuit using nIR microscopy. For a die that is 725 microns thick, at least 625 microns of silicon is removed before nIR microscopy can be used.

Thinning the die for analysis of an IC requiring or benefiting from back side access is usually accomplished by first globally thinning, wherein the silicon is thinned across the entire die surface. The silicon is globally thinned to allow viewing of the active circuit from the back side of the die using nIR microscopy. Mechanical polishing and chemical-mechanical polishing are two example methods for global thinning. Using nIR microscopy, an area is identified for accessing a particular area of the circuit.

Another method used for etching semiconductors is wet etching. In a typical wet etch process, a wet chemical solution is introduced to a surface of a semiconductor device. Reactants in the solution diffuse to and react with the surface. The reaction can include the adsorption of the reactants into the surface, and subsequent desorption of reaction byproducts after the reaction takes place. The reaction products diffuse from the surface and are removed. For example, a typical reaction during wet etching of silicon involves the formation of an oxide layer on the silicon surface via the introduction of reactants to the surface which results in oxidation. The oxide layer is subsequently dissolved, effectively etching the surface. This process is commonly known as an oxidation-reduction (redox) reaction.

Wet etching is often used to selectively etch a substrate on which desired features of an integrated circuit have been masked, such as with an applied photoresist. The photoresist can be applied to a silicon surface in a desired pattern. A wet etch process is then applied, and the surface is etched to match the pattern. Although it has experienced widespread use for front side etching of silicon in semiconductor devices, wet etching has been generally inapplicable to back side etching.

SUMMARY OF THE INVENTION

The present invention is exemplified in a number of implementations and applications, some of which are summarized below. According to an example embodiment of the present invention, a semiconductor device having a back side and a circuit side opposite the back side is analyzed. The semiconductor device includes bulk silicon in the back side and epitaxial silicon. A wet etch solution comprising tetramethylammonium hydroxide (TMAH) is directed at the back side. Using the wet etch solution, the back side is selectively etched and an exposed region is formed. The etching is selective to the bulk silicon. When the etching process encounters the epitaxial silicon, the etch rate slows and is used as an endpoint indicator of the selective etching process. Once the etching process is stopped, the circuitry is accessed via the exposed region.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
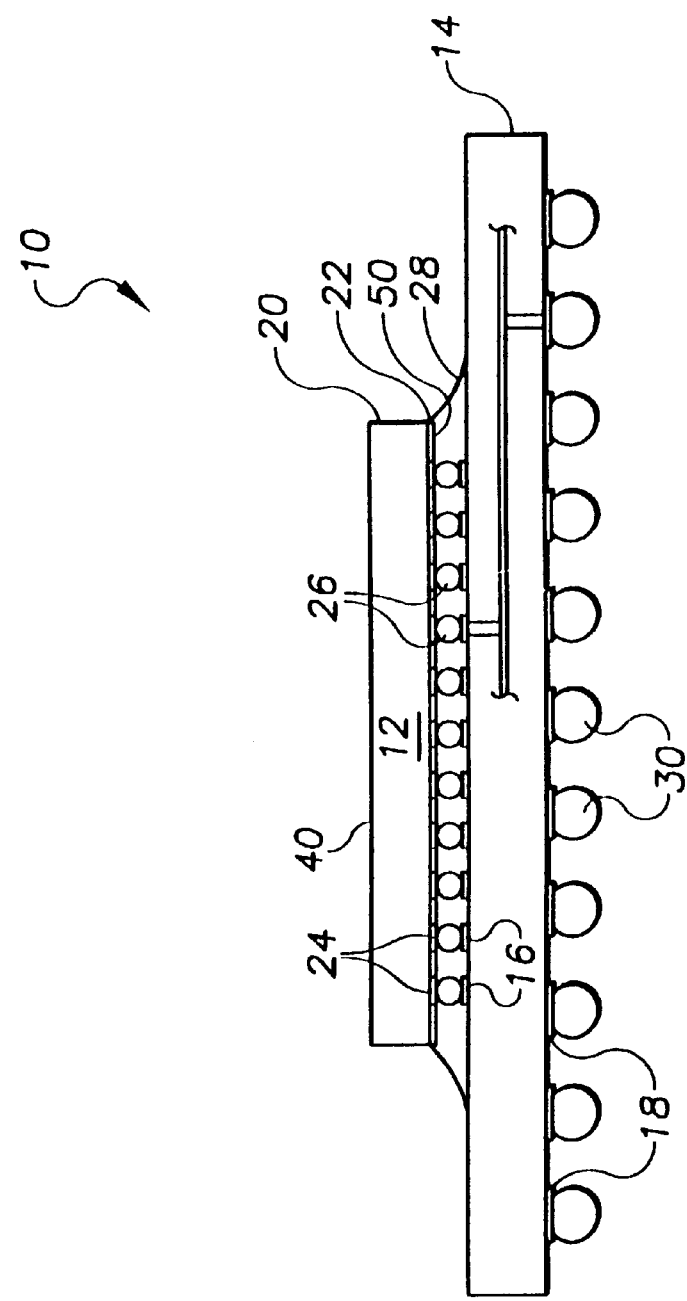
FIG. 1 is a flip-chip type die attached to a package substrate, for use in accordance with the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of semiconductor devices, and the invention has been found to be particularly suited for flip-chip and other devices requiring or benefiting from back side etching. While the present invention is not necessarily limited to such devices, various aspects of the invention may be appreciated through a discussion of various examples using this context.

In connection with the present invention, FIG. 1 shows a side view of an assembly 10 of one type of conventional flip chip type die 12 assembled to a package substrate 14. Flip chip die 12 has a circuit side 50 and a back side 40. The circuit side 50 includes a number of circuit devices formed near the circuit side in a portion of the die known as the epitaxial layer 22. The epitaxial layer 22 has a thickness in the range of 1 to 15 microns. The portion of the die shown above the epitaxial layer is known as the bulk layer 20. A plurality of solder bumps 26 are made on the circuit side 50 at pads 24. The solder bumps 26 are the inputs and outputs to the circuitry associated with the die 12. The flip chip type die 12 is attached to package substrate 14, such as a package for a flip chip via the solder bumps on the die 12. The package substrate 14 includes pads 16 which are arranged to correspond to the pattern of solder bumps on the die 12. The region between integrated circuit 12 and package substrate 14 is filled with an under-fill material 28 to encapsulate the solder bump connections and provide additional mechanical benefits. The pads 16 are coupled via circuitry to pads 18 on the package substrate. Solder bumps 30 are formed on the pads 18. The solder bumps 30 are the inputs and outputs to the circuitry associated with the package substrate 14. In another arrangement (not illustrated), the inputs and outputs to the circuitry associated with the package substrate 14 are implemented as pins rather than solder bumps.

Figure 2:
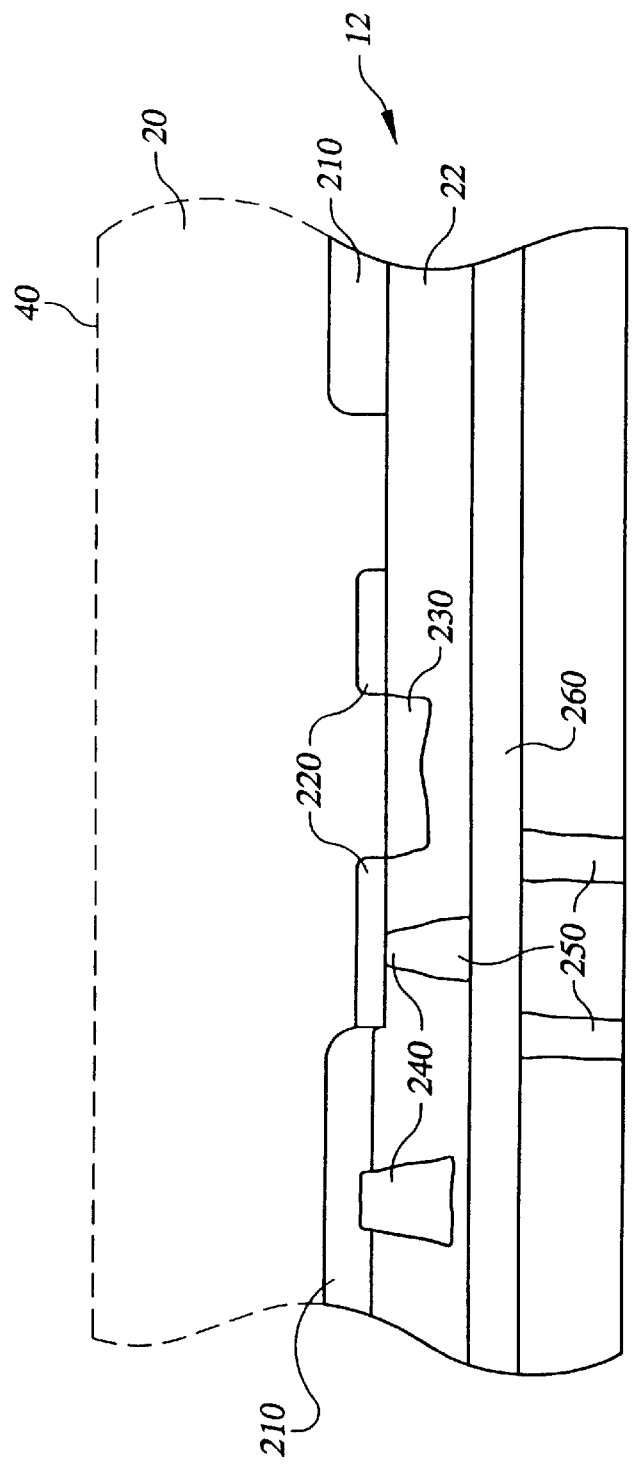
FIG. 2 shows a flip-chip die, such as shown in FIG. 1, having undergone selective wet etch, according to another example embodiment of the present invention.

FIG. 2 shows a portion of a flip-chip type die 12 having undergone wet etch, according to another example embodiment of the present invention. Dashed lines at the top of the device show where silicon in the back side has been removed. Portions of the die including shallow trench isolation 210, source or drain regions 220, and a gate region 230 have been exposed. Further regions, such as a first metal 240, plugs 250, and a second metal 260 may be exposed via additional procedures. In addition, the die 12 may be located in a processing chamber, where etching processes can be performed.

In connection with the present invention, and according to an example embodiment, it has been discovered that the back-side of a semiconductor device can be etched without damaging the die via a selective wet etch process that uses a solution comprising tetramethylammonium hydroxide (TMAH) that is selective to silicon. Various example embodiments of the present invention use TMAH in an aqueous solution (TMAHW) having a water content of about 25% or 15%. Alternatively, TMAH can be used at full strength. Using this recipe, silicon in the back side of a semiconductor device can be etched and an exposed region can be formed without necessarily etching or damaging the circuitry or substrate in the device.

For example, the recipe can be used to remove bulk silicon in the back side of the semiconductor device, and leave portions of a circuit layer intact, such as shown in FIG. 2. Certain regions, such as the source and drain regions 220, may be etched by the TMAH solution, but the etch rate can be monitored to minimize the amount of those regions that is removed. Since the TMAH solution is selective to the silicon, the etch rate slows when the silicon has been removed and epitaxial silicon or other portions of a circuit layer below have been exposed. The slowing of the etch rate can be used as an indication of the endpoint of the etch process. According to a more particular example embodiment, the etch rate of the bulk silicon versus the epitaxial silicon is about 1000:1.

In another example embodiment, a computer arrangement is used and the etch rate is monitored. The computer is arranged to provide an indication of the endpoint of the silicon removal, and to control the etching process. The etch rate may, for instance be correlated to a threshold level defined as a function of the semiconductor device and the etching process. The computer is used to compare the etch rate with the threshold. When the threshold is reached, the etching process is stopped.

Figure 3:
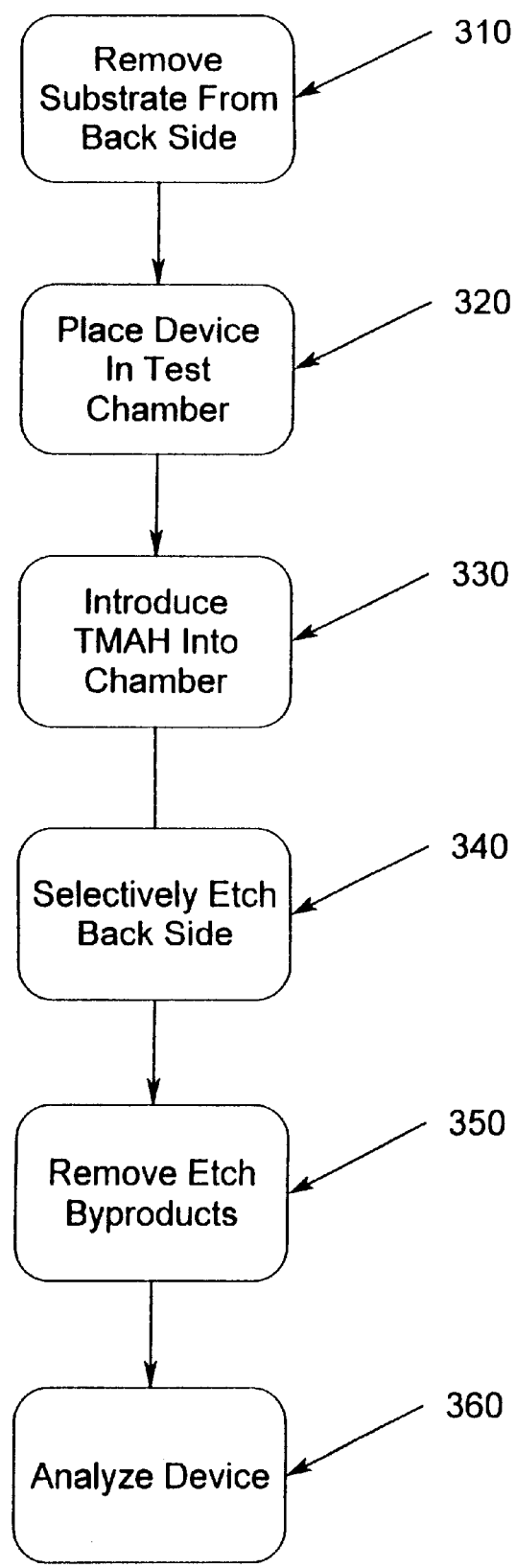
FIG. 3 is a flow diagram of a method for analyzing a semiconductor device, according to another example embodiment of the present invention.

FIG. 3 is a flow chart for a method of analyzing a semiconductor device, according to another example embodiment of the present invention. Substrate is removed from the back side of a semiconductor device at block 310. The device is then placed in a test chamber at block 320. It should be noted, however, that the test chamber is not necessarily required to perform this process. A wet etch solution comprising TMAH is introduced to the device at block 330, and the back side is etched at block 340. The etching step generates byproducts including oxygen that are dissolved and removed, via another aspect of the wet etch process, from the device at block 350. After the device has been etched, it is analyzed via the back side at block 360.

According to another example embodiment of the present invention, a semiconductor device having a back side and a circuit side opposite the back side is delayered. The semiconductor device includes bulk silicon in the back side, epitaxial silicon, and at least one circuit layer in the circuit side. A first wet etch solution comprising tetramethylammonium hydroxide (TMAH) is introduced to the back side. Using the first wet etch solution, bulk silicon in the back side is selectively etched. The wet etch solution leaves the epitaxial silicon and the circuit layer about intact. Once the bulk silicon has been removed, the etch rate slows down or the etching stops. The slowing of the etch rate can be used as an endpoint indicator of the step of selectively etching, and the process is stopped in response to the indication of the endpoint.

In another example embodiment of the present invention involving post-manufacturing failure analysis, a relatively thick oxide mask is patterned over a portion of the back side of a semiconductor device. The mask may be, for instance, about 200 nanometers thick. Using a TMAH wet etch solution, the device is etched. The relatively thick oxide acts to prevent some or all of the back side from being etched, and the portion of the device not having the mask is selectively etched. The etched area is then used as an access path to analyze underlying circuitry.

In still another example embodiment of the present invention, a thin layer of oxide is formed over bulk silicon and a thin layer of silicon is formed thereon. Next, an active region of a semiconductor device such as in a silicon-on-insulator application is formed over the thin silicon layer. In subsequent post-manufacturing failure analysis, TMAH wet etching, as described above, is used to access circuitry within, such as the source and drain regions. The thin layer of oxide is used during the TMAH wet etching as an etch stop.

Other processes can then be performed subsequent to selectively wet etching as described herein. Processes such as subsequent wet etch, dry etch, polishing, or milling can be used to de-layer the device. For instance, a portion of a circuit layer including shallow trench isolation (STI), aluminum, tungsten, a source, a drain, a gate, an oxide, or a metal interconnect can be removed. In addition, an entire circuit layer may be removed to access a portion of the device beneath the layer.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a semiconductor device having a back side and a circuit side opposite the back side, wherein the semiconductor device includes bulk silicon in the back side and also includes epitaxial silicon, the method comprising:
introducing a wet etch solution comprising tetramethylammonium hydroxide (TMAH) to the back side;
using the wet etch solution, selectively etching the back side and forming an exposed region, wherein the etching is selective to bulk silicon; and
using the epitaxial silicon as an endpoint indicator of the step of selectively etching; and
accessing circuitry via the exposed region.

2. A method for analyzing a semiconductor device, according to claim 1, wherein the wet etch solution is selective to the bulk silicon versus the epitaxial silicon at about a 1000:1 ratio.

3. A method for analyzing a semiconductor device, according to claim 1, wherein the semiconductor device includes at least one source region and at least one drain region, and wherein selectively etching the back side includes etching the source and drain regions at a slower rate than etching the bulk silicon.

4. A method for analyzing a semiconductor device, according to claim 1, wherein using the epitaxial silicon as an endpoint indicator of the step of selectively etching comprises:
monitoring the etch rate; and
stopping the selective etching process, responsive to monitoring the etch rate.

5. A method for analyzing a semiconductor device, according to claim 4, wherein the etch rate of the bulk silicon is between about 1000 times faster than the etch rate of the epitaxial silicon.

6. A method for analyzing a semiconductor device, according to claim 4, wherein the etching process is stopped when the etch rate slows to a threshold level defined as a function of the semiconductor device and the etching process.

7. A method for analyzing a semiconductor device, according to claim 6, wherein stopping the etching process responsive to monitoring the etch rate includes using a computer arrangement.

8. A method for analyzing a semiconductor device, according to claim 7, wherein the computer arrangement is adapted to control the wet etch process.

9. A method for analyzing a semiconductor device having a back side and a circuit side opposite the back side, wherein the semiconductor device includes bulk silicon in the back side and also includes epitaxial silicon, the method comprising.
introducing a wet etch solution comprising tetramethylammonium hydroxide (TMAH) to the back side;
using the wet etch solution, selectively etching the back side and forming an exposed region, wherein the etching is selective to bulk silicon; and
using the epitaxial silicon as an endpoint indicator of the step of selectively etching; and accessing circuitry via the exposed region, wherein selectively etching the back side includes
reacting a wet etch solution with substrate in the back side and forming oxide on the back side surface, and dissolving and removing the oxide layer.

10. A method for analyzing a semiconductor device, according to claim 1, wherein introducing a wet etch solution and selectively etching the back side is carried out in a processing chamber.

11. A method for analyzing a semiconductor device having a back side and a circuit side opposite the back side, wherein the semiconductor device includes bulk silicon in the back side and also includes epitaxial silicon, the method comprising:
thinning the back side of the device to about 100 microns prior to selectively etching the back side;
introducing a wet etch solution comprising tetramethylammonium hydroxide (TMAH) to the back side;
using the wet etch solution, selectively etching the back side and forming an exposed region, wherein the etching is selective to bulk silicon;
using the epitaxial silicon as an endpoint indicator of the step of selectively etching; and
accessing circuitry via the exposed region.

12. A method for analyzing a semiconductor device, according to claim 1, wherein introducing a wet etch solution includes introducing a solution comprising aqueous tetramethylammonium hydroxide having a water content of about 25%.

13. A method for analyzing a semiconductor device, according to claim 1, wherein introducing a wet etch solution includes introducing a solution comprising aqueous tetramethylammonium hydroxide having a water content of about 15%.

14. A method for analyzing a semiconductor device, according to claim 1, wherein introducing a wet etch solution includes introducing a solution composed primarily of tetramethylammonium hydroxide.

15. A method for analyzing a semiconductor device having a back side and a circuit side opposite the back side, wherein the semiconductor device includes bulk silicon in the back side and also includes epitaxial silicon, the method comprising:

introducing a wet etch solution comprising tetramethylammonium hydroxide (TMAH) to the back side;

reacting the wet etch solution with substrate in the back side and selectively etching bulk silicon in the back side and forming an oxide layer, wherein the etching is selective to the bulk silicon;

dissolving and removing the oxide layer produced by the reaction;

monitoring the etch rate and detecting a slowing of the etch rate; and responsive to detecting a slowing of the etch rate, stopping the etch process.

16. A method for de-layering a semiconductor device having a back side and a circuit side opposite the back side, wherein the semiconductor device includes bulk silicon in the back side and also includes epitaxial silicon, the method comprising:

introducing a first wet etch solution comprising tetramethylammonium hydroxide (TMAH) to the back side;

using the first wet etch solution, selectively etching the back side and removing bulk silicon, wherein the etching is selective to bulk silicon; and using the epitaxial silicon as an endpoint indicator of the step of selectively etching.

17. A method for de-layering a semiconductor device, according to claim 16, wherein the device includes at least one circuit layer, further comprising removing at least a portion of the circuit layer subsequent to selectively etching the back side.

18. A method for de-layering a semiconductor device, according to claim 17, wherein removing at least a portion of a circuit layer comprises selectively removing at least one of: shallow trench isolation (STI), aluminum, tungsten, a source, a drain, a gate, an oxide, and a metal interconnect.

19. A method for analyzing a semiconductor device having a back side and a circuit side opposite the back side, wherein the semiconductor device includes bulk silicon in the back side and also includes epitaxial silicon, the method comprising:

patterning an oxide having a thickness of about 200 nanometers over at least a portion of the back side of a semiconductor device;

using a TMAH wet etch solution and etching the back side of the device, wherein the patterned portion is not etched; and accessing a portion of the underlying circuitry.

\* \* \* \* \*

UNITED STATES PATENT AND TRADEMARK OFFICE
CERTIFICATE OF CORRECTION

PATENT NO.    : 6,428,718 B1
DATED         : August 6, 2002
INVENTOR(S)   : Birdsley et al.

It is certified that error appears in the above-identified patent and that said Letters Patent is hereby corrected as shown below:

Column 6,
Line 19, "comprising." should read -- comprising: --.
Line 26, the statement starting with "accessing" should begin on the next line, line 27.

Signed and Sealed this

Third Day of December, 2002

JAMES E. ROGAN
*Director of the United States Patent and Trademark Office*